United States Patent
Hou et al.

(10) Patent No.: US 10,077,462 B2
(45) Date of Patent: Sep. 18, 2018

(54) MICROFLUIDIC MICROBE DETECTION AND ISOLATION

(71) Applicants: THE BROAD INSTITUTE, INC., Cambridge, MA (US); MASSACHUSETTS INSTITUTE OF TECHNOLOGY, Cambridge, MA (US); THE GENERAL HOSPITAL CORP, Boston, MA (US)

(72) Inventors: Han Wei Hou, Singapore (SG); Jongyoon Han, Bedford, MA (US); Roby Bhattacharyya, Cambridge, MA (US); Deb Hung, Lexington, MA (US)

(73) Assignees: The Broad Institute, Inc., Cambridge, MA (US); Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 176 days.

(21) Appl. No.: 14/775,341

(22) PCT Filed: Mar. 14, 2014

(86) PCT No.: PCT/US2014/027569
§ 371 (c)(1),
(2) Date: Sep. 11, 2015

(87) PCT Pub. No.: WO2014/152643
PCT Pub. Date: Sep. 25, 2014

(65) Prior Publication Data
US 2016/0032350 A1 Feb. 4, 2016

Related U.S. Application Data

(60) Provisional application No. 61/799,378, filed on Mar. 15, 2013.

(51) Int. Cl.
*C12Q 1/24* (2006.01)
*B01L 3/00* (2006.01)
(Continued)

(52) U.S. Cl.
CPC .......... *C12Q 1/24* (2013.01); *B01L 3/502753* (2013.01); *G01N 15/0255* (2013.01);
(Continued)

(58) Field of Classification Search
CPC ....... B01L 2300/088; B01L 2300/0861; B01L 2300/08; B01L 3/502753; B01L 3/5027; B01L 3/50
(Continued)

(56) References Cited

U.S. PATENT DOCUMENTS

| 8,208,138 B2 | 6/2012 | Papautsky et al. |
| 2009/0014360 A1 | 1/2009 | Toner et al. |
| 2011/0070581 A1 | 3/2011 | Gupta et al. |

FOREIGN PATENT DOCUMENTS

WO 2011109762 A1 9/2011

OTHER PUBLICATIONS

Hou, Han Wei, et al, Isolation and retrieval of circulating tumor cells using centrifugal forces, Nature, Feb. 2013, 3: 1259, pp. 1-8. (Year: 2013).*

(Continued)

*Primary Examiner* — Christine T Mui
(74) *Attorney, Agent, or Firm* — Johnson, Marcou & Isaacs, LLC

(57) ABSTRACT

A method and microfluidic device useful for isolating microbes from a blood sample which includes introducing the blood sample into the sample inlet of a spiral microfluidic device; and introducing a second fluid into the sheath inlet of the microfluidic device, wherein the spiral channel terminates in a microbe outlet and a waste outlet, and (Continued)

wherein the spiral channel includes a length, height, and a width that define an aspect ratio adapted to isolate any microbes present in the sample along a first portion of the spiral channel terminating at the microbe outlet, and to isolate red blood cells and leukocytes along a second portion of the spiral channel terminating at the waste outlet; and collecting the microbes from the microbe outlet, thereby isolating the microbes.

25 Claims, 9 Drawing Sheets

(51) Int. Cl.
  *G01N 15/02*    (2006.01)
  *G01N 15/00*    (2006.01)
(52) U.S. Cl.
  CPC .......... B01L 2200/0636 (2013.01); *B01L 2200/0652* (2013.01); *B01L 2300/088* (2013.01); *B01L 2300/0816* (2013.01); *B01L 2300/0861* (2013.01); *B01L 2400/0487* (2013.01); *G01N 2015/0065* (2013.01); *G01N 2015/0288* (2013.01)

(58) Field of Classification Search
  USPC .................... 422/50, 500, 400, 401
  See application file for complete search history.

(56) References Cited

OTHER PUBLICATIONS

Hou, Han Wei, et al, Supplementary Information: Isolation and retrieval of circulating tumor cells using centrifugal forces, Nature, Feb. 2013, 3: 1259, pp. 1-7. (Year: 2013).*
Kuntaegowdanahalli S. et al, Inertial microfluidics for continuous particle separation in spiral microchannels, Lab Chip, 2009, 9, 2973-2980. (Year: 2009).*
International Preliminary Report on Patentability dated Sep. 24, 2015 for PCT/US2014/027569, dated Sep. 24, 2015, 9 pgs.
International Search Report and Written Opinion dated Oct. 1, 2014 for PCT/US2014/027569, dated Oct. 1, 2014, pp. 1-20.
Zelenin, "Bacteria Isolation from Whole Blood Sepsis Diagnostics", In: 15th International Conference on Miniaturized Systems for Chemistry and Life Sciences 2011 (MicroTAS 2011), published Apr. 2012, pp. 518-520.

* cited by examiner

FIG. 2

- Obtain whole blood sample

- Dilute whole blood in buffer

- Introduce diluted blood into sample inlet/introduce buffer into sheath inlet

- Collect blood waste from blood cell outlet and collect bacteria from sorted bacteria outlet

- Perform bacteria culture and/or molecular analysis on sorted bacteria

Whole blood    Spiral eluent

MICROFLUIDIC MICROBE DETECTION AND ISOLATION

CROSS REFERENCE TO RELATED APPLICATION

This application is the U.S. National Stage of International Application No. PCT/US2014/027569, filed Mar. 14, 2014, published in English under PCT Article 21(2), which claims the priority benefit of the earlier filing date of U.S. Provisional Application No. 61/799,378, filed Mar. 15, 2013, which is hereby specifically incorporated herein by reference in its entirety.

FEDERALLY SPONSORED RESEARCH OR DEVELOPMENT

This invention was made with Government support under Grant Nos. U54 AI057159 and 272200900018C awarded by the National institutes of Health, and Grant No. N66001-11-1-4182 awarded by the Defense Advanced Research Projects Agency (DARPA) of the Department of Defense. The Government has certain rights in the invention.

TECHNICAL FIELD

This disclosure relates to microfluidics and more particularly to microfluidic separation of pathogens from samples.

BACKGROUND

The development of molecular diagnostics has revolutionized care in most medical disciplines except infectious disease, where they have failed to play a widespread, transforming role. The reliance on slow culture methods is particularly frustrating in the current crisis of antibiotic resistance as the development of molecular tools to rapidly diagnose the inciting pathogen and its drug resistance profile would transform the management of bacterial, fungal, viral, and parasitic infections, guiding rapid, informed drug treatment in an effort to decrease mortality, control health care costs, and improve public health control of escalating resistance among pathogens. In U.S. hospitals alone, 1.7 million people acquire nosocomial bacterial infection and 99,000 die every year, with 70% of these infections due to bacteria resistant to at least one drug at estimated annual cost of $45 billion (Klevens et al., 2002. Public Health Rep. 2007; 122(2):160-6; Klevens et al., Clin Infect Dis. 2008; 47(7): 927-30; Scott, "The Direct Medical Costs of Healthcare-Associated Infection in U.S. Hospitals and the Benefits of Prevention." In: *Division of Healthcare Quality Promotion NCfP, Detection and Control of Infectious Diseases*, editor. Atlanta: CDC, 2009). However, the problem is not limited to the U.S. and microbial resistance now impacts the majority of common bacterial infections globally. Global spread of methicillin-resistant *S. aureus* (MRSA), multi-drug resistant tuberculosis (MDR-TB), and increasingly drug resistant Gram-negative organisms prompted the formulation of an action plan focusing on surveillance, prevention and control, research and product development (US action plan to combat antimicrobial resistance. Infect Control Hosp Epidemiol. 2001; 22(3):183-4). However, minimal progress has been made on any of these fronts.

Prompt administration of the appropriate antibiotic has repeatedly been shown to minimize mortality in patients with severe bacterial infections, whether within the hospital setting with nosocomial pathogens such as *E. faecium, S. aureus, K. pneumoniae, A. baumanii, P. aeruginosa*, and *Enterobacter* species, or in resource-poor settings with pathogens such as tuberculosis (TB) (Harbarth et al., Am J Med. 2003; 115(7):529-35; Harries et al., Lancet. 2001; 357(9267):1519-23; Lawn et al., Int J Tuberc Lung Dis. 1997; 1(5):485-6). However, because current diagnostic methods involving culture and sub-culture of organisms can take several days or more to correctly identify both the organism and its drug susceptibility pattern, physicians have resorted to increasing use of empiric broad-spectrum antibiotics, adding to the selective pressure for resistance and increasing the associated health-care costs. A point of care diagnostic to rapidly (e.g., less than 1 hour) detect pathogens and their resistance profiles is urgently needed and could dramatically change the practice of medicine. Some effort into designing DNA- or PCR-based tests has resulted in tools that are able to identify pathogens rapidly with low detection limits. However, global use of these tools is currently limited due to cost and demand for laboratory infrastructure and to the inherent insensitivity of PCR-based methods in the setting of crude samples that are not easily amenable to the required enzymology. Molecular approaches to determining drug resistance have been even more limited, available for some organisms (e.g., MRSA, TB) in very limited ways, based on defining the genotype of the infecting bacteria relative to known resistance conferring mutations. This method however, requires fairly comprehensive identification of all resistance conferring single nucleotide polymorphisms (SNPs) for the test to have high sensitivity (Carroll et al., Mol Diagn Ther. 2008; 12(1):15-24).

One key limitation to broad adoption of molecular diagnostic tests in clinical infectious disease is the inhibitory effects of bodily fluids such as blood upon many of the reactions required for molecular detection. Isolating or enriching pathogens away from host cells would greatly numerous downstream detection and characterization assays, such as nucleic acid hybridization or amplification tests that could be used to determine the identity or antibiotic susceptibility of the pathogen.

SUMMARY

The present disclosure is based, at least in part, on the development of microfluidic devices that can be used to separate microbes from samples with a vast excess of larger blood cells. Thus disclosed is a microfluidic device of use in separating microbes from samples, such as blood samples.

Also disclosed is a method of isolating one or more microbes from a blood sample comprising red blood cells and leukocytes, the method comprising introducing the blood sample into the sample inlet of a disclosed microfluidic device having at least one spiral channel; and introducing a second fluid into the sheath inlet of the microfluidic device at a flow rate at least about 5 to about 15 times of the blood sample flow rate, wherein the spiral channel terminates in a microbe outlet and a waste outlet, and wherein the spiral channel comprises a length, height, and a width that define an aspect ratio adapted to isolate any microbes present in the sample along a first portion of the spiral channel terminating at the microbe outlet, and to isolate red blood cells and leukocytes along a second portion of the spiral channel terminating at the waste outlet; and collecting the microbes from the microbe outlet, thereby isolating the microbes.

The disclosed microfluidic devices include at least one spiral channel having: a first end; a second end; a channel height; a channel width; and a channel length. The spiral channel has a length, a height and a width that define an aspect ratio adapted to isolate any microbes present in the sample along a first portion of the spiral channel and to isolate red blood cells and leukocytes along a second portion of the spiral channel. The first end includes a sample inlet and a sheath inlet, the sample inlet having a width of between about 50 µm and about 100 µm and the sheath inlet having a width of between about 300 µm and about 700 µm. The second end includes a microbe outlet and a waste outlet, the microbe outlet having a width of between about 175 µm and about 600 µm and the waste outlet having a width of between about 175 µm and about 600 µm. The channel height is about 50 µm to about 120 µm. The channel width is about 300 µm to about 700 µm. The channel length is between about 5 cm and about 20 cm.

The microbe recovery may be at least 65%, e.g., about 75%. Platelets may be separated with an efficiency of about 40%. The second fluid may be phosphate buffered saline (PBS). The microbes may be isolated along the radially outermost portion of the spiral channel to the microbe outlet. The leukocytes and/or red blood cells may be isolated along the radially innermost portion of the spiral channel to the waste outlet. The hematocrit level (volume percentage (%) of red blood cells) in the blood sample may be about 15%. The blood sample may comprise one or more microbes, red blood cells, leukocytes, and platelets, wherein the microbes may be separated from any leukocytes in the sample. The method may further comprise analyzing the microbes after collection. The microbes may undergo a single Dean cycle migration prior to exiting the channel at the microbe outlet.

Also provided herein are methods of isolating microbes using these devices, and methods for diagnosing and treating a subject based on the detection, identification, or determination of drug sensitivity of microbes from samples using these devices.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The foregoing and other features of this disclosure will become more apparent from the following detailed description of a several embodiments, which proceeds with reference to the accompanying figures.

DESCRIPTION OF DRAWINGS

FIG. 2 is a flow diagram of an exemplary method used to isolate microbes from a blood sample using a microfluidic device schematically illustrated in FIG. 1A.

DETAILED DESCRIPTION OF SEVERAL EMBODIMENTS

Figure 1A:
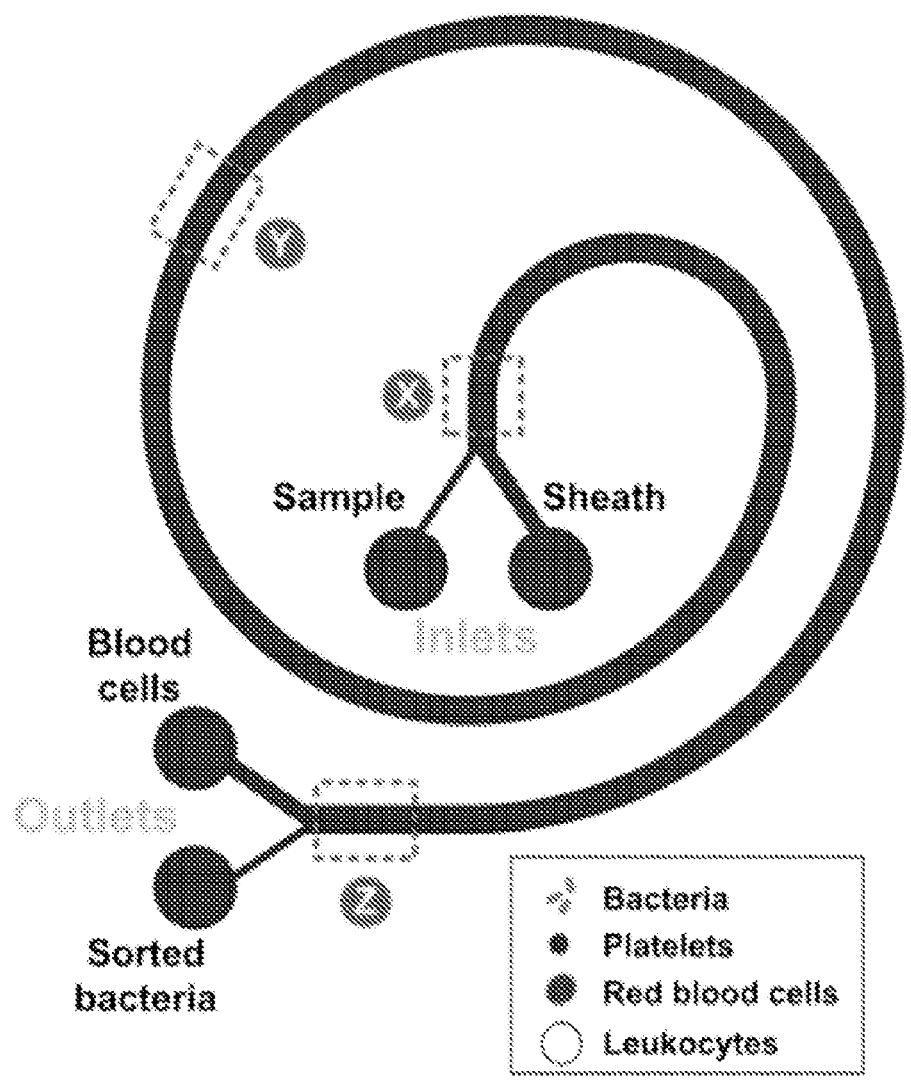
FIG. 1A is a schematic diagram of an exemplary high throughput microbe isolation microfluidic device.
Figure 1B:
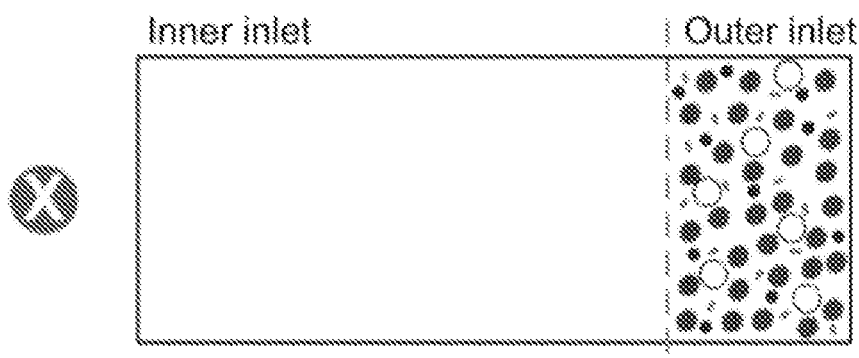
FIG. 1B is a schematic illustration of the bacteria, platelet, red blood cell, and leukocyte distribution across the channel at point X in FIG. 1A.

This disclosure is generally related to microfluidic devices and the uses of such devices to detect and/or isolate one or more rare pathogenic microbes, such as bacteria present in whole blood and/or a blood fraction, for example as low as about, 10-100 organisms per mL of whole blood. Whole blood contains an excess of cellular material such as red blood cells ("RBCs"): about $10^9$/mL; platelets: about $10^8$/mL; and leukocytes: about $10^6$/mL. This excess material present in blood and even blood fractions creates significant challenges in the separation and molecular analysis of these rare pathogens, such as pathogens that may be present in the blood in small numbers, such as present as low as 10-100 per mL of whole blood. To address this issue, the disclosed microfluidic devices were developed.

The devices disclosed herein include one or more channels, such as spiral channels, at least two outlets and one or more inlets, and typically feature two outlets and two inlets, for example two outlets and two inlets per channel. In some embodiments, the first inlet is a sample inlet, for example for introducing whole blood, or a blood fraction, which may contain microbes, into the device. In some embodiments, the second inlet is a sheath inlet, for example for introducing a sheath fluid, such as a buffered solution, into the device.

In use, the microbes are separated into a first outlet, and remaining particulate, such as red blood cells, leukocytes, and any platelets not isolated in the first outlet, of the sample and thus flows to a second outlet. Each inlet, outlet, and channel has a length, and height/width customizable to the channel. Each channel has a length and a cross section of a height and a width defining an aspect ratio adapted to isolate the targeted microbes along at least one first portion of the cross section of the channel and to isolate the remaining cells, e.g., red blood cells and leukocytes, against a second portion of the cross section of the channel. As used herein, an aspect ratio is the ratio of a channel's height divided by its width and provides the appropriate cross section of the channel to allow the microbes to flow along at least one portion of the cross section of the channel to a first outlet, and the remaining cells to flow along a different (e.g., second, third, fourth, etc.) part or cross section of the channel and not to the same outlet as the microbes, such as to a distinct (e.g., second, third, fourth, etc.) outlet. For example, as shown herein, aspect ratios of between about 0.5 and about 0.1 can be used, for example about 0.1, 0.15, 0.2, 0.25, 0.3, 0.35, 0.4, 0.45, or about 0.5, such as between about 0.1 and 0.3, about 0.3 and about 0.5, about 0.2 and about 0.5, about 0.15 and 0.35, about 0.25 and about 0.35, about 0.25 and about 0.45 and the like. In some embodiments, the ratio of the leukocytes and/or red blood cells to channel height is about 0.05 to about 0.2, such as about, 0.05, 0.06, 0.07, 0.08, 0.09, 0.10, 0.11, 0.12, 0.13, 0.14, 0.15, 0.16, 0.17, 0.18, 0.19, or about 0.20, such as between about 0.05 and 0.1, about 0.08 and about 0.18 about 0.09 and about 0.11, about 0.9 and about 0.15, or about 0.1 and about 0.2. In particular embodiments the ratio of the leukocytes and/or red blood cells to channel height is about 0.1. In some embodiments, the ratio of microbe diameter to channel height is less than about 0.05, such as less than about 0.04, 0.03, 0.02, or 0.01. In particular embodiments, the ratio of microbe diameter to channel height is less than about 0.03.

The second portion of the cross section of the channel is distanced from the first portion. The first outlet is attached to the first portion while the second outlet is attached to the second portion. In some embodiments, the device is configured as a spiral and the first portion is on the outer wall of the spiral and the second portion is on the inner wall of the spiral. A sample can be introduced into the device, such as through the sample inlet using a variety of techniques known to those of ordinary skill in the art. For example, the sample can be introduced using a syringe and/or a pump. Similarly, a sheath fluid can be introduced into the device, for example through a sheath inlet, using a variety of techniques known to those of ordinary skill in the art. For example, the sheath fluid can be introduced using a syringe and/or a pump.

Figure 1C:
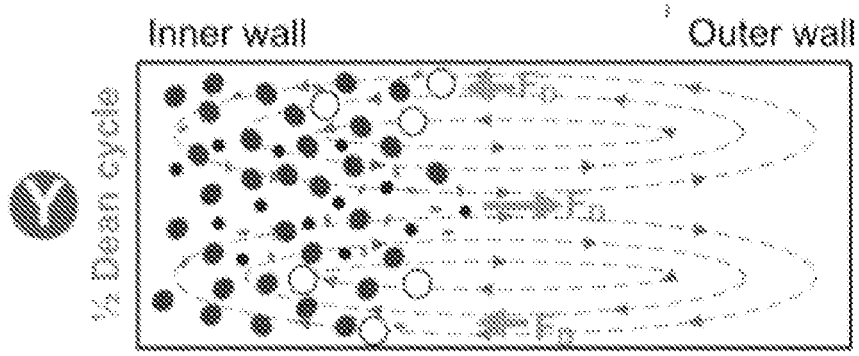
FIG. 1C is a schematic illustration of the bacteria, platelet, red blood cell, and leukocyte distribution across the channel at point Y in FIG. 1A.
Figure 1D:
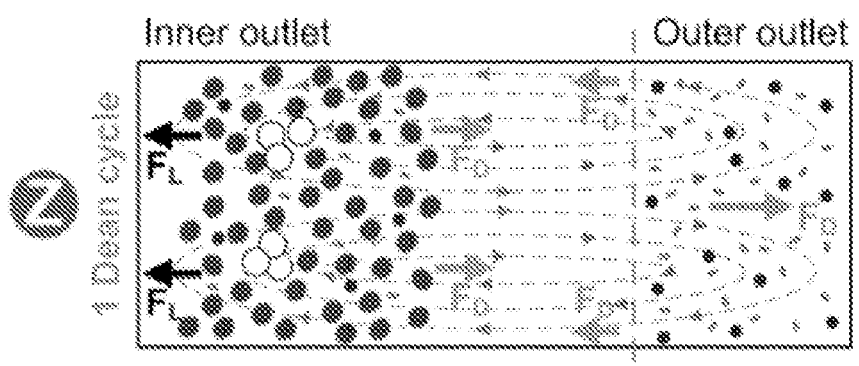
FIG. 1D is a schematic illustration of the bacteria, platelet, red blood cell, and leukocyte distribution across the channel at point Z in FIG. 1A.
Figure 3:
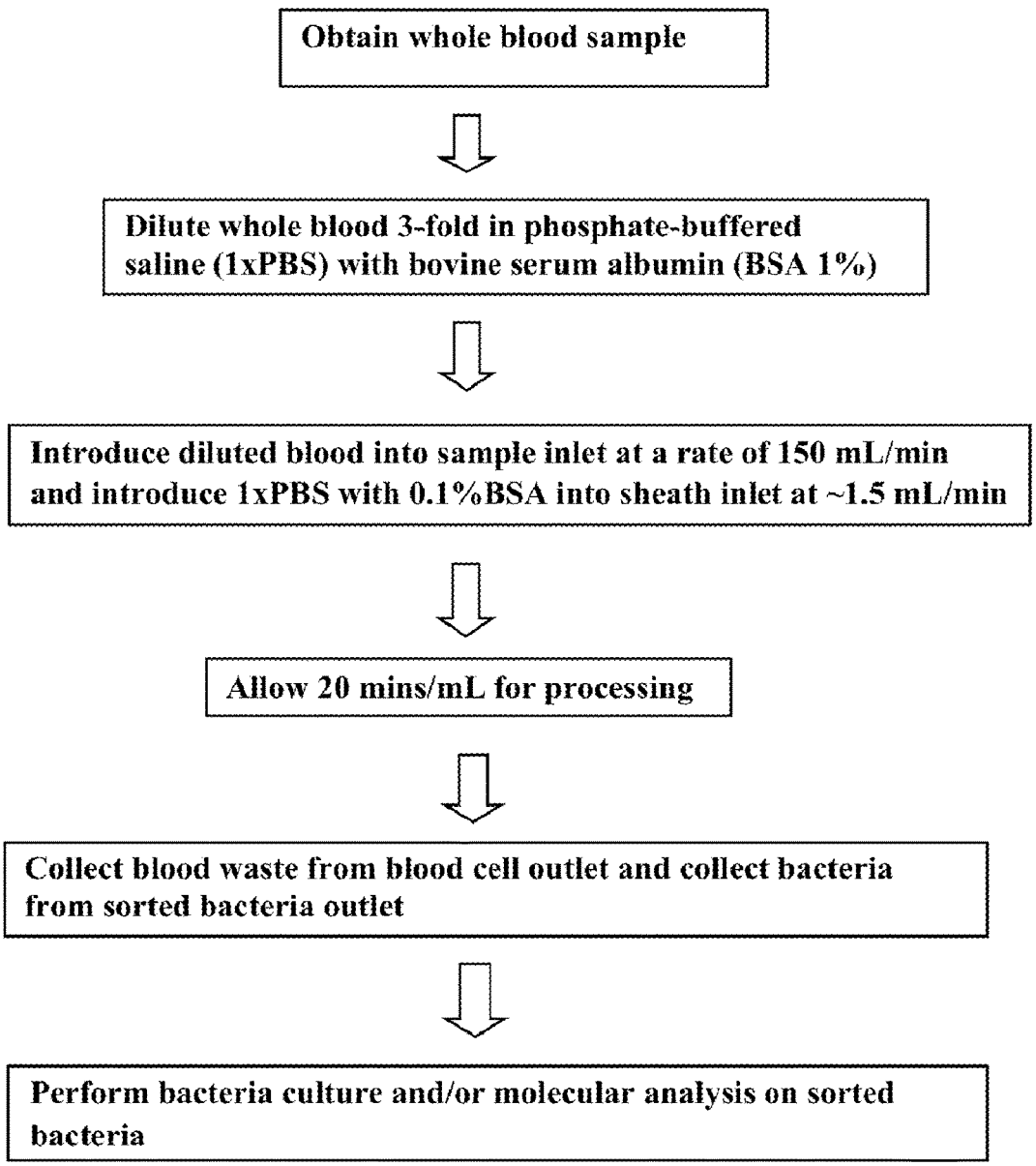
FIG. 3 is a flow diagram of an exemplary method used to isolate microbes from a blood sample using a microfluidic device schematically illustrated in FIG. 1A.

To achieve this high-throughput microbe separation from blood, the microfluidic device exploits the size difference between hematologic cells, e.g., RBCs at ~8 μm discoid; leukocytes at ~7-12 μm and pathogenic microbes at <3 μm. In curvilinear channels, fluids experience Dean vortices, i.e., two symmetrical counter-rotating vortices, at the top and bottom and across the channel cross section due centrifugal acceleration directed radially outward. The magnitude of these secondary flows is characterized by a non-dimensional Dean number (De). Particles flowing in these curvilinear channels experience a lateral drag force ($F_D$) because of these transverse Dean flows, entraining and driving them along the direction of flow within these vortices. This motion translates to the particles moving back and forth along the channel width between the inner and outer walls with increasing downstream distance when visualized from the top or bottom. The particle's lateral migration can be defined in terms of 'Dean cycle' (DC). For example, a particle which is initially positioned near the micro-channel outer wall migrates to the inner wall at a given distance downstream after completing ½ Dean cycle (DC 0.5). This particle returns back to the original position near the channel outer wall after a full Dean cycle (DC 1). For a given micro-channel length, the particles can thus undergo multiple Dean cycle migrations with increasing flow rates (Re). The length for a complete Dean cycle migration (LDC) can be approximated as:

$$L_{DC} \sim 2w+h, \quad (1)$$

where w is the micro-channel width and h is the channel height. Referring to FIGS. 1C-1D, as the bacteria, platelets, RBCs, and leukocytes enter the microfluidic device, the particles are centralized in the outer wall region. As the particles reach a DC 0.5, the particles are centralized in the inner wall region. However, as the particles reach DC 1, the small particles, e.g., bacteria and small platelets, are centralized in the outer wall portion due to the Dean drag force, while the larger particles, e.g., the RBCs and leukocytes are centralized in inner wall portion due to the inertial lift force. The appropriate flow rate necessary to ensure that the particles of interest undergo a complete Dean cycle is dependent on many factors including the dimension of the microfluidic device and the high-through put needs of a particular application. Apart from Dean drag force, larger particles and cells in curvilinear micro-channels also experience appreciable inertial lift forces ($F_L$) near the inner wall, resulting in particle focusing. This particle focusing position is dependent on the ratio of inertial lift to Dean drag forces ($F_L/F_D$), which scales exponentially with particle size. It is particularly effective for particles having a size comparable to the micro-channels dimension, e.g., particle diameter ap/h~0.1 where ap is the particle/cell diameter and h is the micro-channel's height.

The microfluidic device uses both inertial focusing to direct the larger cells, e.g., the leukocytes and RBCs near one portion of the wall, e.g., the inner wall, and Dean drag to focus the smaller bacteria and platelets along the second portion of the wall, e.g., the outer wall. For example, as the sample travels through the channel, the bacterial and blood cells initiate migration along the Dean vortex towards the inner channel. The larger particles, e.g., leukocytes and RBCs equilibrate near the inner wall due to the strong inertial force that prevents them from migrating due to the Dean drag, while the smaller platelets and bacteria continue to flow along the Dean vortex back towards the outer wall.

Referring to FIGS. 1A-1D, which in no way limit the configuration of the device, in some embodiments, the microfluidic device comprises, or consists of, a 2-inlet, 2-outlet spiral micro-channel having a width of between about 300 μm and about 700 μm, such as about 300 μm, 325 μm, 350 μm, 375 μm, 400 μm, 425 μm, 450 μm, 475 μm, 500 μm, 525 μm, 550 μm, 575 μm, 600 μm, 625 μm, 650 μm, 675 μm, 700 μm, for example, about 450 μm to about 500 μm, about 475 μm to about 525 μm, about 400 μm to about 600 μm, or about 375 μm to about 625 μm. In particular embodiments the micro-channel has a width of about 500 μm. In some embodiments, the micro-channel has a height of between about 50 μm and 120 μm, such as about 50 μm, 55 μm, 60 μm, 65 μm, 70 μm, 75 μm, 80 μm, 85 μm, 90 μm, 95 μm, 100 μm, 105 μm, 110 μm, 115 μm, or 120 μm, for example between about 60 μm and about 100 μm, about 65 μm and about 95 μm, about 70 μm and about 90 μm, or about 75 μm and about 85 μm. In particular embodiments the micro-channel has a height of about 80 μm. In some embodiments, the micro-channel has a length of between about 5 cm and 20 cm, such as about 5, 5.5, 6.0, 6.5, 7, 7.5, 8, 8.5, 9.0, 9.5, 10, 10.5, 11, 11.5, 12, 12.5, 13.0, 13.5, 14, 14.5, 15, 15.5, 16.0, 16.5, 17, 17.5, 18, 18.5, 19.0, 19.5, or 20 cm, such as between about 9 cm and about 11 cm, about 7.5 cm and about 13.5 cm, about 6 cm and about 14 cm, about 12.5 cm and about 16.5 cm, about 5 cm, about 10 cm or about 9.5 cm and about 19.5 cm, about 7 cm and about 13 cm, or about 9.5 cm and about 10.5 cm. In particular embodiments the micro-channel has a total length of about 10 cm. In some embodiments, the sample inlet has a width of between about 50 µm and about 100 µm, such as about 50 µm, 55 µm, 60 µm, 65 µm, 70 µm, 75 µm, 80 µm, 85 µm, 90 µm, 95 µm, 100 µm (measured from the outer channel wall), such as between about 70 µm and about 80 µm, about 55 µm and about 90 µm, about 65 µm and about 85 µm, about 75 µm and about 100 µm, or about 60 µm and about 90 µm. In some embodiments, the sheath inlet has a width of between about 300 µm and about 700 µm, such as about 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, or 700 µm (measured from the inner channel wall), such as between about 420 µm and about 430 µm, about 320 µm and about 530 µm, about 350 µm and about 650 µm, about 400 µm and about 500 µm, about 375 µm and about 450 µm, about 400 µm and about 600 µm, or about 400 µm and about 600 µm. In particular embodiments, the sample inlet can have a width of about 75 µm (measured from the outer channel wall) while the sheath inlet can have a width of about 425 µm (measured from the inner channel wall). The sample inlet is located at the outer side of the channel, while the sheath inlet is fixed at the inner side of the channel, relative to the rotation of the spiral. As RBCs constitute >99% of the cellular components of whole blood, significant RBC removal is imperative for efficient and meaningful isolation of rare pathogens for diagnostic applications. In some embodiments, the microbe, for example bacterial, outlet has a width of between about 175 µm and about 600 µm, such as about 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm (measured from the outer channel wall), such as between about 190 µm and 210 µm, about 195 µm and about 205 µm, about 175 µm and 225 µm, about 200 µm and about 400 µm, about 200 µm and 500 µm, or about 250 µm and about 650 µm. In some embodiments, the waste outlet has a width of between about 200 µm and about 600 µm, such as about 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm (measured from the inner channel wall), such as between about 420 µm and about 430 µm, such as between about 190 µm and 510 µm, about 295 µm and about 505 µm, about 175 µm and 525 µm, about 300 µm and about 600 µm, about 400 µm and 500 µm, or about 250 µm and about 350 µm. In particular embodiments, the bacteria outlet has a width of about 200 µm (measured from the outer channel wall) and the waste outlet has a width of about 300 µm (measured from the inner channel wall). This design ensures efficient bacteria recovery while minimizing RBCs contamination in the bacteria outlet. Because of the designed bifurcated outlet, the target population, e.g., the bacteria, can then be collected based on their size. The channel dimensions are selected such that the larger particles undergo inertial focusing, while the migration of the smaller cells, e.g., bacteria, is affected by the Dean drag (i.e., only the leukocytes and RBCs satisfy the ap/h~0.1 ratio). Because the microbes are not affected by the Dean drag, they continue to circulate along the Dean vortex towards the outer wall. The disclosed devices are arranged to form at least about 1.0 spirals, such as at least 1.0, 1.1, 1.2, 1.3, 1.4, 1.5, 1.6, 1.7, 1.8, 1.9 or at least about 2.0 spirals. In particular embodiments, the disclosed devices are arranged to form at least about 1.5 spirals. The spirals have a radius of curvature between about 0.3 to about 1.5 cm, such as about 0.3, 0.4, 0.5, 0.6, 0.7, 0.8, 0.9, 1.0, 1.1, 1.2, 1.3, 1.4, and 1.5 cm. By way of example, in a specific example of a device with 1.5 spirals, the outer loop of approximately 1.0 spirals has a radius of curvature of about 1 cm with the inner semicircle having a radius of curvature of about 0.42 cm. In some embodiments, the disclosed devices are arranged to form less than about 10 spirals, such as less than about 9, 8, 7, 6, 5, 4, 3, or 2 spirals. Given the guidance presented in the specification, one of ordinary skill in the art can produce a disclosed spiral device for the separation of microorganisms, such as bacteria from blood or blood fractions.

Referring to FIG. 2, the devices described herein can be used in a method to separate microbes from remaining cells, e.g., blood cells and leukocytes, in a sample. In one embodiment, whole blood is diluted between about 2-fold and about 5-fold, such as 3-fold, in a buffered solution, such as an isotonic buffered solution, for example in phosphate-buffered saline (1×PBS) with bovine serum albumin (BSA, 0.1%) so that its viscosity was compatible with rapid processing in the spiral micro-channel. Sheath fluid, e.g., any physiologically compatible fluid, can be used to pinch the whole blood at the inlet, thus confining the blood sample to a narrow region across the channel width. This ensures that the cells start to migrate from approximately the same location. In some embodiments, the diluted blood sample is loaded into a delivery mechanism and injected into the sample inlet at a rate of about 100 µL/min to about 200 µL/min, such as about 100 µL/min, 125 µL/min, 150 µL/min, 175 µL/min or 200 µL/min, for example between about 125 µL/min and about 175 µL/min. In some embodiments sheath fluid is injected, into the sheath inlet at about 1.0 mL/min to about 2.0 mL/min, such as about 1.0 mL/min, 1.25 mL/min, 1.50 mL/min, 1.75 mL/min or 2.0 mL/min, for example between about 1.25 mL/min and about 1.75 mL/min. In particular embodiments, the diluted blood sample is loaded into a delivery mechanism, e.g., a syringe, and injected into the sample inlet at a rate of about 150 uL/min, while sheath fluid, such as 1×PBS with 0.1% BSA, is injected, such as with a pump, into the sheath inlet at ~1.5 mL/min. By calculating the appropriate flow rates, it is ensured that the microbes undergo a full Dean cycle migration at the outlet ensuring that the microbes are focused near the outer wall while the blood cells are focused near the inner wall. Achieving separation requires time for processing, e.g., about 20 mins/mL of whole blood before blood waste, e.g., red blood cells and leukocytes can be collected from the waste outlet while microbes can be collected from the sorted bacteria outlet. One advantage of using this technique is the ability to process very high hematocrit samples as compared with other microfluidic devices, e.g. 10%, 15%, and/or 20%. This reduces the overall sample preparatory steps and analysis time. After microbe collection, further culture and/or molecular analysis can be performed on the sorted bacteria.

The microfluidic device described herein can be used to detect, separate, and/or isolate a microbe from a sample, such as a whole blood of blood fraction sample. The sample of cells can be, for example, a biological sample, such as blood (e.g., whole blood), plasma, peritoneal fluid, lymph, spinal fluid, urine, tissue, and the like. The sample can also be a cell culture sample. In a particular aspect, the sample is a blood sample (e.g., a whole blood sample). The blood sample can have a low hematocrit (e.g., about 1-10%), or a high hematocrit (e.g., about 20-50%).

In one aspect, the device is used in a method of detecting one or more pathogenic microbes in a blood sample. The method includes introducing a blood sample into at least one inlet of a microfluidic device comprising one or more channels wherein each channel has a length and a cross-section consisting of a height and a width defining an aspect ratio adapted to isolate the microbes along at least one portion of the cross-section of the channel, wherein microbes flow along a first portion of each channel to a first outlet and the blood cells flow along a second portion of each channel to a second outlet. The method can further include collecting the separated microbes from the first outlet. In certain embodiments, the microfluidic device can further include an expansion region for improved visualization. The microfluidic device described herein can be used to detect, separate, and/or isolate microbes from a sample of cells. The sample of cells can be, for example, a biological sample, such as blood (e.g., whole blood), plasma, peritoneal fluid, lymph, spinal fluid, urine, tissue, and the like. The sample can also be a cell culture sample. In a particular aspect, the sample is a blood sample (e.g., a whole blood sample). The blood sample can have a low hematocrit (e.g., about 1-10%), or a high hematocrit (e.g., about 20-50%).

Analysis of Samples—Methods of Diagnosis and Treatment

After microbe collection, further culture and/or molecular analysis can be performed on the sorted bacteria. For example, the methods described herein can be used, e.g., for identifying a pathogen in a sample, e.g., a clinical sample, as well as determining the drug sensitivity of a pathogen based on expression profile signatures of the pathogen. Thus the methods herein can further include one or more of the following: further purification or enrichment of the microbes in the sample; RNA isolation from the microbes; DNA isolation from the microbes; protein isolation from the microbes; analysis of RNA, DNA, and/or protein from the microbes; identification of microbes in the sample; identification of drug sensitivity of the microbes in the sample. Methods known in the art can be used in combination with this method, for example, those described in PCT/US2011/026092. In some embodiments, the separated microbes are tested for antibiotic resistance, such as resistance to one or more of aminoglycosides (such as amikacin, gentamicin, kanamycin, neomycin, netilmicin, streptomycin, tobramycin, and paromomycin); ansamycins (such as geldanamycin, and herbimycin); carbacephems (such as loracarbef, ertapenem, doripenem, imipenem/cilastatin, and meropenem); cephalosporins (such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and ceftobiprole); glycopeptides (such as teicoplanin and vancomycin); macrolides (such as azithromycin, clarithromycin, dirithromycin, erythromycin, roxithromycin, troleandomycin, telithromycin, and spectinomycin); monobactams (such as aztreonam); penicillins (such as amoxicillin, ampicillin, azlocillin, carbenicillin, cloxacillin, dicloxacillin, flucloxacillin, mezlocillin, meticillin, nafcillin, oxacillin, penicillin, piperacillin, and ticarcillin); polypeptides (such as bacitracin, colistin, and polymyxin b); quinolones (such as ciprofloxacin, enoxacin, gatifloxacin, levofloxacin, lomefloxacin, moxifloxacin, norfloxacin, ofloxacin, trovafloxacin, grepafloxacin, and sparfloxacin); sulfonamides (such as mafenide, prontosil (archaic), sulfacetamide, sulfamethizole, sulfanilimide (archaic), sulfasalazine, sulfisoxazole, trimethoprim, and trimethoprim-sulfamethoxazole); tetracyclines (such as demeclocycline, doxycycline, minocycline, oxytetracycline, and tetracycline); and others (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin, thiamphenicol, and tinidazole).

Thus the methods described herein include methods for diagnosing, selecting treatments for, and treating subjects, e.g., mammalian (preferably human) subjects. The methods of diagnosis include obtaining a sample from a subject; isolating microbes from the sample using a method described herein; and identifying the microbes present in the sample. The methods of selecting a treatment for or treating a subject include obtaining a sample from a subject; isolating microbes from the sample using a method described herein; performing one or both of identifying the microbes present in the sample and/or determining drug sensitivity of the microbes present in the sample; and optionally administering a drug to which the microbes are sensitive.

Any method known in the art for identifying microbes or determining drug sensitivity can be used, e.g., those described in PCT/US2011/026092, which is incorporated herein by reference in its entirety, and PCR-based techniques (with appropriate reagents to inactivate DNA polymerase inhibitors in blood), mass spectrometry, direct nucleic acid hybridization, antibody-based detection methods such as enzyme-linked immunosorbent assays, or culture (Expert Rev Med Devices 2009; 6: 641; Anal Bioanal Chem 2009; 394: 731; Nat Biotechnol 2008; 26: 317; Proc Nat'l Acad Sci USA 2012; 109: 6217 all of which are incorporated herein by reference in their entirety).

Although the methods described herein have been exemplified for use with blood or blood-derived samples, the methods can also be used on other fluids, e.g., biological fluids, e.g., urine, sputum, joint fluid, cerebrospinal fluid, biliary fluid, pleural fluid, peritoneal fluid, or pericardial fluid.

In addition, although the present methods have been exemplified with *E. coli*, any microbes of less than 3 µm can be isolated using the methods described herein. Exemplary microbes include pathogens such as bacterial pathogen and fungal pathogens amongst others and any bacteria that causes disease (pathogenic bacteria). Examples in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophile, Aeromonas veronii biovar sobria* (*Aeromonas sobria*), and *Aeromonas caviae*), *Anaplasma phagocytophilum, Anaplasma marginate Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*), *Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp.

Coxiella burnetii, Corynebacterium sp. (such as, Corynebacterium diphtheriae, Corynebacterium jeikeum and Corynebacterium), Clostridium sp. (such as Clostridium perfringens, Clostridium difficile, Clostridium botulinum and Clostridium tetani), Eikenella corrodens, Enterobacter sp. (such as Enterobacter aerogenes, Enterobacter agglomerans, Enterobacter cloacae and Escherichia coli, including opportunistic Escherichia coli, such as enterotoxigenic E. coli, enteroinvasive E. coli, enteropathogenic E. coli, enterohemorrhagic E. coli, enteroaggregative E. Coli and uropathogenic E. coli) Enterococcus sp. (such as Enterococcus faecalis and Enterococcus faecium) Ehrlichia sp. (such as Ehrlichia chafeensia and Ehrlichia canis), Erysipelothrix rhusiopathiae, Eubacterium sp., Francisella tularensis, Fusobacterium nucleatum, Gardnerella vaginalis, Gemella morbillorum, Haemophilus sp. (such as Haemophilus influenzae, Haemophilus ducreyi, Haemophilus aegyptius, Haemophilus parainfluenzae, Haemophilus haemolyticus and Haemophilus parahaemolyticus, Helicobacter sp. (such as Helicobacter pylori, Helicobacter cinaedi and Helicobacter fennelliae), Kingella kingii, Klebsiella sp. (such as Klebsiella pneumoniae, Klebsiella granulomatis and Klebsiella oxytoca), Lactobacillus sp., Listeria monocytogenes, Leptospira interrogans, Legionella pneumophila, Leptospira interrogans, Peptostreptococcus sp., Mannheimia hemolytica, Moraxella catarrhalis, Morganella sp., Mobiluncus sp., Micrococcus sp., Mycobacterium sp. (such as Mycobacterium leprae, Mycobacterium tuberculosis, Mycobacterium paratuberculosis, Mycobacterium intracellulare, Mycobacterium avium, Mycobacterium bovis, and Mycobacterium marinum), Mycoplasm sp. (such as Mycoplasma pneumoniae, Mycoplasma hominis, and Mycoplasma genitalium), Nocardia sp. (such as Nocardia asteroides, Nocardia cyriacigeorgica and Nocardia brasiliensis), Neisseria sp. (such as Neisseria gonorrhoeae and Neisseria meningitidis), Pasteurella multocida, Plesiomonas shigelloides. Prevotella sp., Porphyromonas sp., Prevotella melaninogenica, Proteus sp. (such as Proteus vulgaris and Proteus mirabilis), Providencia sp. (such as Providencia alcalifaciens, Providencia rettgeri and Providencia stuartii), Pseudomonas aeruginosa, Propionibacterium acnes, Rhodococcus equi, Rickettsia sp. (such as Rickettsia rickettsii, Rickettsia akari and Rickettsia prowazekii, Orientia tsutsugamushi (formerly: Rickettsia tsutsugamushi) and Rickettsia typhi), Rhodococcus sp., Serratia marcescens, Stenotrophomonas maltophilia, Salmonella sp. (such as Salmonella enterica, Salmonella typhi, Salmonella paratyphi, Salmonella enteritidis, Salmonella cholerasuis and Salmonella typhimurium), Serratia sp. (such as Serratia marcesans and Serratia liquifaciens), Shigella sp. (such as Shigella dysenteriae, Shigella flexneri, Shigella boydii and Shigella sonnei), Staphylococcus sp. (such as Staphylococcus aureus, Staphylococcus epidermidis, Staphylococcus hemolyticus, Staphylococcus saprophyticus), Streptococcus sp. (such as Streptococcus pneumoniae (for example chloramphenicol-resistant serotype 4 Streptococcus pneumoniae, spectinomycin-resistant serotype 6B Streptococcus pneumoniae, streptomycin-resistant serotype 9V Streptococcus pneumoniae, erythromycin-resistant serotype 14 Streptococcus pneumoniae, optochin-resistant serotype 14 Streptococcus pneumoniae, rifampicin-resistant serotype 18C Streptococcus pneumoniae, tetracycline-resistant serotype 19F Streptococcus pneumoniae, penicillin-resistant serotype 19F Streptococcus pneumoniae, and trimethoprim-resistant serotype 23F Streptococcus pneumoniae, chloramphenicol-resistant serotype 4 Streptococcus pneumoniae, spectinomycin-resistant serotype 6B Streptococcus pneumoniae, streptomycin-resistant serotype 9V Streptococcus pneumoniae, optochin-resistant serotype 14 Streptococcus pneumoniae, rifampicin-resistant serotype 18C Streptococcus pneumoniae, penicillin-resistant serotype 19F Streptococcus pneumoniae, or trimethoprim-resistant serotype 23F Streptococcus pneumoniae), Streptococcus agalactiae, Streptococcus mutans, Streptococcus pyogenes, Group A streptococci, Streptococcus pyogenes, Group B streptococci, Streptococcus agalactiae, Group C streptococci, Streptococcus anginosus, Streptococcus equismilis, Group D streptococci, Streptococcus bovis, Group F streptococci, and Streptococcus anginosus Group G streptococci), Spirillum minus, Streptobacillus moniliformi, Treponema sp. (such as Treponema carateum, Treponema petenue, Treponema pallidum and Treponema endemicum, Tropheryma whippelii, Ureaplasma urealyticum, Veillonella sp., Vibrio sp. (such as Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela and Vibrio furnisii), Yersinia sp. (such as Yersinia enterocolitica, Yersinia pestis, and Yersinia pseudotuberculosis) and Xanthomonas maltophilia among others. Examples of fungal pathogens in accordance with the disclosed methods include without limitation Trichophyton rubrum, T. mentagrophytes, Epidermophyton floccosum, Microsporum canis, Pityrosporum orbiculare (Malassezia furfur), Candida sp. (such as Candida albicans), Aspergillus sp. (such as Aspergillus fumigatus, Aspergillus flavus and Aspergillus clavatus), Cryptococcus sp. (such as Cryptococcus neoformans, Cryptococcus gattii, Cryptococcus laurentii and Cryptococcus albidus), Histoplasma sp. (such as Histoplasma capsulatum), Pneumocystis sp. (such as Pneumocystis jirovecii), and Stachybotrys (such as Stachybotrys chartarum) among others.

In specific examples, exemplary microbes include E. faecium, A. baumanii, Enterobacter species, Escherichia coli, Pseudomonas aeruginosa, Klebsiella pneumoniae, Stenotrophomonas maltophilia, Mycobacterium tuberculosis, Staphylococcus aureus, and Enterococcus faecalis. For example, any microbe listed in Table 1 or Table 6 of PCT/US2011/026092 can be isolated.

The following examples are provided to illustrate certain particular features and/or embodiments. These examples should not be construed to limit the invention to the particular features or embodiments described.

EXAMPLES

Example 1

Purpose

While leukocytes constitute ~0.1% of all blood cells (~5 million per mL), they still greatly outnumber clinically relevant pathogen concentrations in blood (~10 cells per mL), and removal of nucleated leukocytes would significantly reduce the background noise for subsequent molecular analysis.

Method

After characterizing the flow rate conditions and sample hematocrit for DC 1 in the microfluidic device a pure population of leukocytes (obtained by RBCs lysis) and RBCs were pumped through the device and high-speed imaging (6400 frames per second) was used to capture their flow positions near the outlet region.

Results

Figure 4:
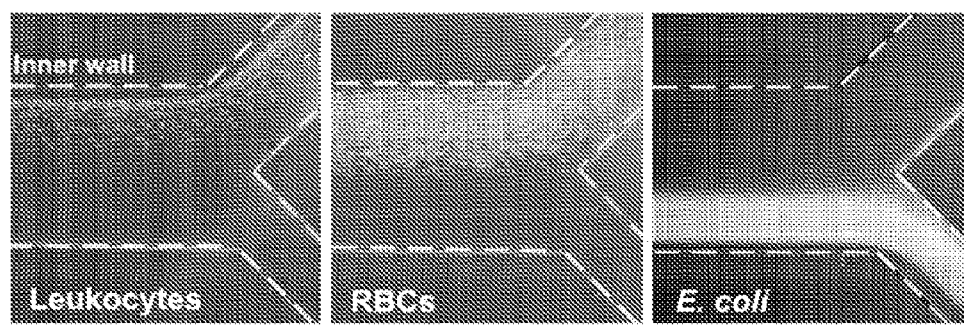
FIG. 4 is a series of average composite images indicating the lateral position of the RBCs, leukocytes, and microbes, e.g., *E. coli*, at the outlet of the microfluidic device.

Referring to FIG. 4, an image of the outlet bifurcation illustrates the focusing of leukocytes and RBCs along the inner wall and the microbes, e.g., FITC-conjugated *E. coli* along the along the outer channel. The larger leukocytes and RBCs experienced appreciable inertial forces (ap/h~0.1 ratio) during the lateral migration and focused near the inner wall. The dashed lines indicate position of the channel walls. The RBC focusing band was broader than leukocytes as expected due to high RBC concentration (~15% hct) causing steric crowding and secondary cell-cell interactions. The FITC-conjugated *Escherichia coli* (*E. coli*) bioparticles (Invitrogen Inc., USA) were solely affected by Dean forces and migrated as a tight band (<200 lam wide) towards the outer wall region.

Conclusion

Compared to other inertial-based microfluidic microbe separation approaches, this technique operates at a much higher throughput as a 3× dilution of whole blood constitutes a 15% hematocrit input sample, translating to a processing time of ~20 minutes for 1 mL of whole blood (at 150 µL min-1 for sample flow rate).

Example 2

Method

Whole blood samples stained with immunofluorescence markers (CD41a for platelets, CD45 for leukocytes) and spiked with *E. coli* bioparticles (~$10^6$/mL) were processed separately using the microfluidic device to quantify bacteria and hematologic cellular components recovery from blood at DC 1. Samples were collected from the bacteria and waste outlets and analyzed using flow cytometry (FACS).

Results

Figure 5:
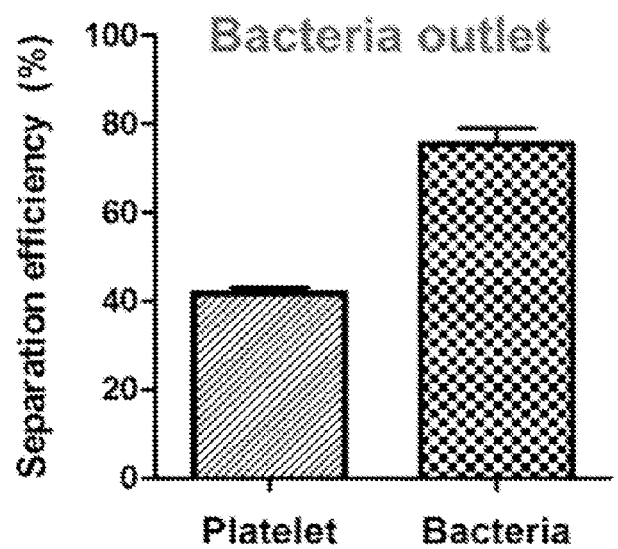
FIG. 5 is a bar graph illustrating recovery efficiency of the microfluidic device. Recovery (or separation) efficiency for RBCs was greater than 99% removal from the final sample, and about 100% removal of WBCs.

Referring to FIG. 5, FACS analysis indicates a recovery efficiency of about 75% and about 40% for the bacteria and platelets, respectively, in the sorted samples collected from the bacteria outlet and the decrease in recovery could be attributed to the high RBC background which hinders the complete Dean migration of bacteria towards the outer channel wall. Platelet recovery was also lower (~40%) at the bacteria outlet possibly due to the larger cell size (~2-3 µm), which would result in higher Stokes' drag as they traverse laterally across the channel width. RBC contamination was minimal with ~$10^3$-$10^4$-fold RBC reduction, and complete leukocyte removal was also achieved in the bacteria outlet as confirmed by FACS.

Example 3

Method

To study the bacterial recovery using this technique, different concentrations of *E. coli* (clinical strain) were spiked into 1 mL of whole blood sample and processed by the device. Sorted samples collected from the bacteria outlet were then centrifuged and resuspended in a smaller volume (~100 µL), followed by culture on agar plates overnight for quantification of colony forming units (CFU).

Results

Figure 6:
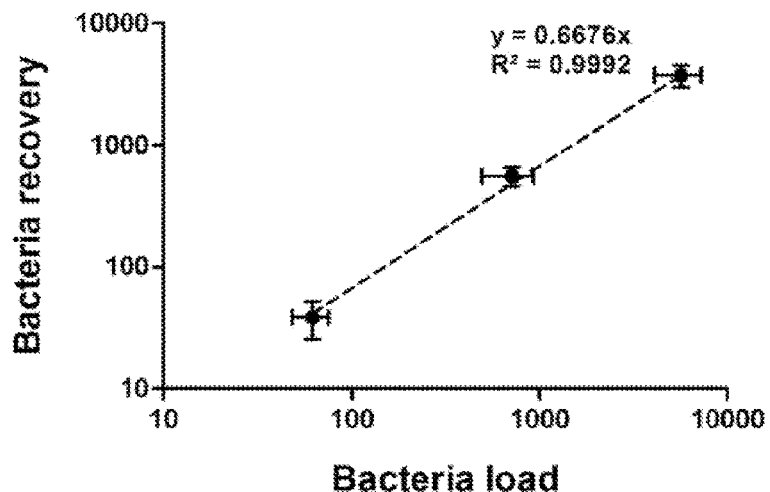
FIG. 6 is a graph illustrating the bacteria recovery as compared to bacteria load of the methods using the microfluidic device.

Referring to FIG. 6, a recovery plot (log scale) indicates a high bacteria recovery (>65%) over a range of bacterial loads (*E. coli*) spiked in 1 mL of whole blood. FIG. 5 shows recovery at the bacteria outlet for different *E. coli* load concentrations ($10^2$-$10^4$ per mL). High bacteria recovery (>65%) was achieved at these low bacteria concentrations, illustrating minimal cell loss and the potential of the device to process clinically relevant blood samples. In particular, the high flow rates used in the system prevent settling and non-specific binding of bacteria to the syringe and tubing, which is an important concern for detection of rare pathogens in blood.

Example 4

Method

To simulate bacterial detection in clinical settings, we processed 1 mL of blood samples spiked with different strains of bacteria (*E. coli*, *Pseudomonas aeruginosa* (*P. aerug.*), *Enterococcus faecalis*, and *Staphylococcus aureus* (*S. aureus*)) at physiological concentrations (~10 organisms/mL), followed by plating the sorted samples collected at the bacteria outlet.

Results

Figure 7:
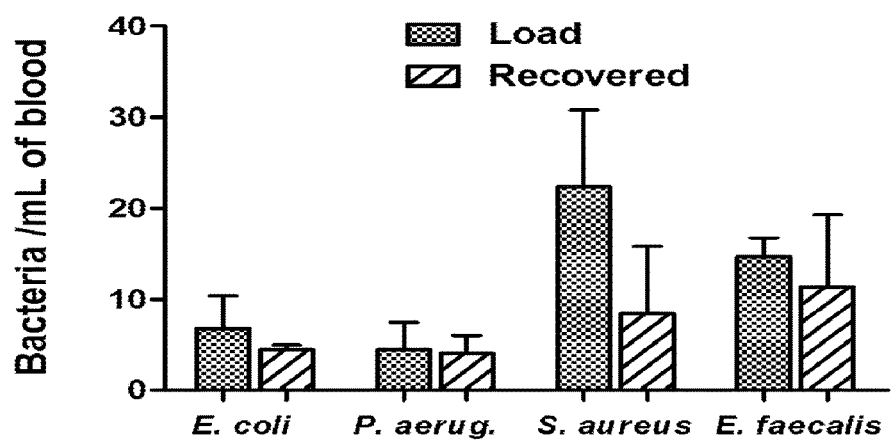
FIG. 7 is a bar graph demonstrating the comparison between bacterial load and recovery across four types of bacteria.

Referring to FIG. 7 and

As shown in Table 1, in all samples loaded at this low concentration, bacteria were successfully detected as colony-forming units (FIG. 7), demonstrating the ability of our technique to reproducibly isolate small numbers of pathogens from whole blood despite a large excess of RBCs (~$10^9$/mL).

As shown in Table 1, in all cases where the small number of bacteria was loaded into the sorting device, a detectable fraction was recovered from the bacteria outlet (by colony forming units on a culture plate).

|  | Pathogenic strain | | | |
| --- | --- | --- | --- | --- |
|  | E. coli | P. aerugs. | S. aureus | E. faecalis |
| Sample size (n) | 5 | 5 | 5 | 5 |
| Detection (%) | 100 | 100 | 100 | 100 |

Example 5

Method

Whole blood was diluted 3-fold in phosphate-buffered saline (1×PBS) with bovine serum albumin (BSA, 0.1%) so that its viscosity was compatible with rapid processing in the spiral micro-channel. In the trial described, the blood sample was spiked with a known quantity of bacteria to measure efficiency of recovery. This diluted blood sample, with bacteria, was loaded into a syringe and pumped into the sample inlet at a rate of 150 uL/min, while sheath fluid (1×PBS with 0.1% BSA) was pumped into the sheath inlet at 1.5 mL/min.

Bacterial recovery was assessed in one of two ways. First, quantitative recovery was determined by plating the cells to determine colony-forming units (cfu). By comparing cfu in the bacterial outlet to cfu in the sample used to spike the blood initially, a quantitative recovery fraction was obtained. Second, the compatibility of the bacterial stream from this device with downstream molecular analysis was tested using RNA hybridization via the Nanostring assay (*Nat Biotechnol* 2008; 26: 317, which is incorporated by reference herein in its entirety), which has utility in microbial diagnostics, both for organism identification and for detection of antibiotic susceptibility profiles (*Proc Nat'l Acad Sci USA* 2012; 109: 6217, which is incorporated by reference herein in its entirety). Eluate from the bacterial outlet was directly processed in the Nanostring assay as described (*Proc Nat'l Acad Sci USA* 2012; 109: 6217) with no further modifications. Briefly, the bacterial outlet was mixed with lysis buffer (Qiagen RLT buffer), hybridized with Nanostring capture and reporter probesets, and processed according to manufacturer's protocols. The Nanostring assay yields a fluorescent readout if a specific RNA sequence is present in the assay (and assay conditions are such that it can be unambiguously recognized by hybridization).

Results

After 20 minutes of processing, 1 mL of whole blood generated 14-15 mL of solution at the bacterial outlet, due to 3-fold initial dilution prior to loading, 10-fold dilution of the sample with sheath fluid within the device, and roughly 50% fractionation between the blood cell outlet and the bacterial outlet. Fractional recovery efficiency is shown in FIG. 2 B-C at higher organism burdens (100-10,000 organisms per mL of whole blood), where we recover >65% of bacteria over a range of starting concentrations. White blood cells are essentially completely depleted from the bacterial outlet stream, and red blood cells are depleted by over 1000-fold.

While it is challenging to estimate the true bacterial burden in a bloodstream infection, best estimates put this number in the range of 10 to 100 organisms per mL for many common pathogens (*PlosONE* 2012; 7:e31126, *J Clin Microbiol* 1984; 20:618, *Chest* 2009; 136:832). To test its utility in this clinically relevant regime, this device was therefore tested at even lower bacterial load. When lower organism burdens were used (10 bacteria per mL), bacteria were recovered in all 20 experimental replicates (100% detection of cfu) across 4 different species of common bloodstream pathogens (FIG. 7). At these concentrations, cellular components of blood are present at $10^8$-fold excess of bacteria, yet the bacteria can still be reproducibly collected in the bacterial outlet of this device, while these cellular components are depleted as above.

Figure 8:
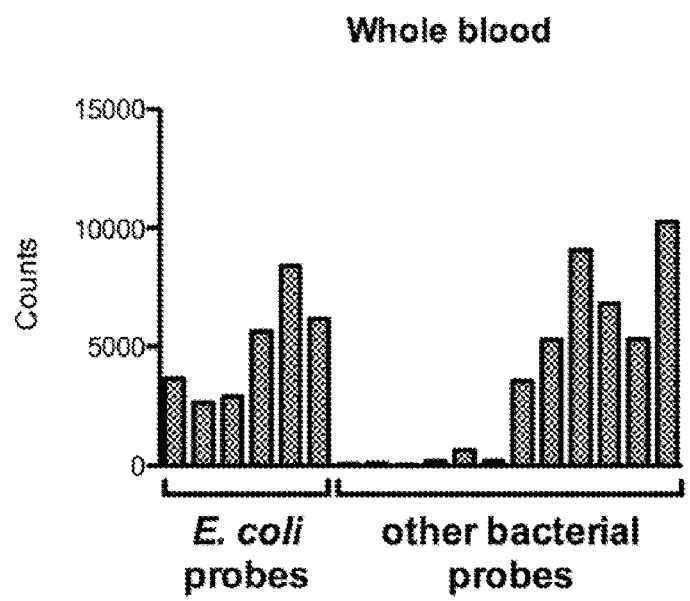
FIG. 8 is a bar graph demonstrating the reactivity of *E. coli* probes as opposed to other bacterial probes at the bacterial outlet for a sample of whole blood with bacteria processed through the device.
Figure 9:
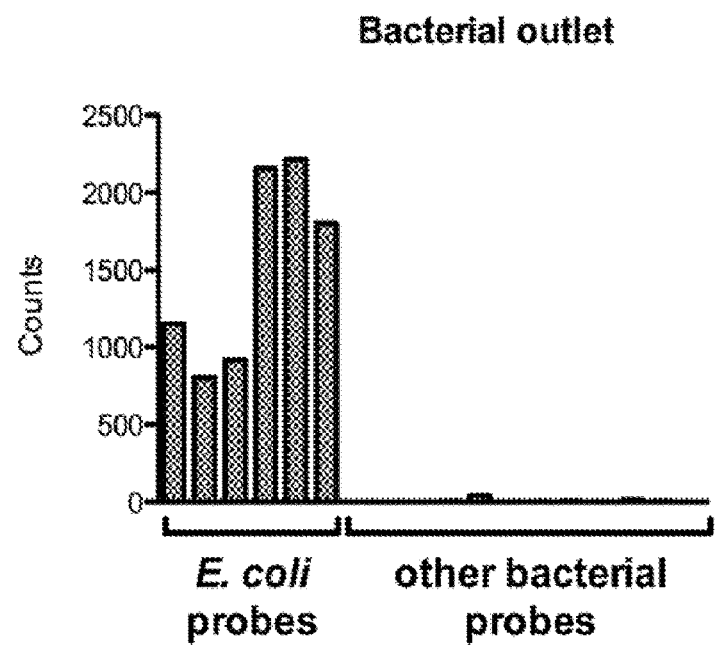
FIG. 9 is a bar graph demonstrating the number of *E. coli* probes as opposed to other bacterial probes present at the bacterial outlet.

Whole blood impairs many molecular diagnostic techniques. For instance, Nanostring, the RNA hybridization technique described above, does not permit direct recognition from blood without extensive sample preparation, including isolation and purification of nucleic acids per manufacturer's protocol. However, this spiral micro-channel device permits specific recognition of microbes using RNA hybridization via Nanostring directly from the bacterial outlet, without any additional processing. For example, referring to FIG. 8, when run directly on whole blood, Nanostring is unable to identify the bacteria as *E. coli* due to high background levels from nonspecific probes. Referring to FIG. 9, the eluate from the bacterial outlet permits unambiguous identification of the *E. coli* that were spiked into the initial whole blood sample. In both plots, each bar on the x-axis corresponds to a single Nanostring probe that recognizes a specific RNA sequence, while the y-axis represents normalized fluorescence units for each probe. As indicated below the x-axis, the first 6 probes recognize RNA sequences from *E. coli*, while the subsequent 12 probes recognize other bacterial species (*Klebsiella pneumoniae*, *P. aeruginosa*, and *S. aureus*).

Example 6

Method

This test was carried out in a similar manner to Example 5, but at a lower concentration of bacteria. A schematic of the experimental design is shown in the top panel of FIG. 10. Whole blood, spiked with a known quantity of bacteria (100 or 1000 cfu/mL of *E. coli*), was diluted 3-fold in phosphate-buffered saline (1×PBS) with bovine serum albumin (BSA, 0.1%) so that its viscosity was compatible with rapid processing in the spiral micro-channel. This diluted blood sample, with bacteria, was loaded into a syringe and pumped into the sample inlet at a rate of 150 uL/min, while sheath fluid consisting of 1×PBS with 0.1% BSA was pumped into the sheath inlet at ~1.5 mL/min. Bacterial recovery was assayed using the Nanostring hybridization assay per protocol to detect ribosomal RNA (rRNA), as described in Example 5 above.

Results

Figure 10:
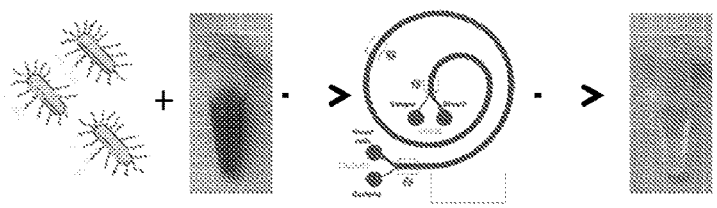
FIG. 10 shows the use high throughput microbe isolation microfluidic device for organism identification by rRNA detection on a Nanostring® platform. Using the disclosed device organism identification can be made at a concentration at least as low as 100-1000 cfu/mL.
Figure 10:
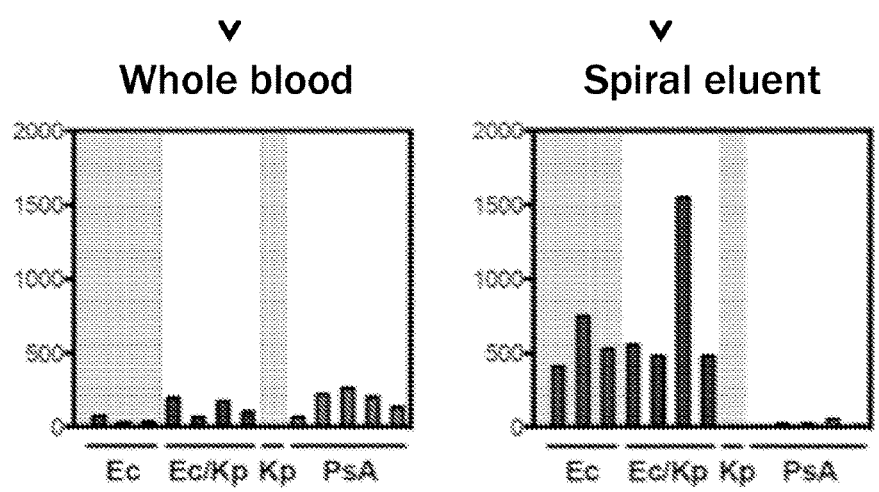
Figure 10:
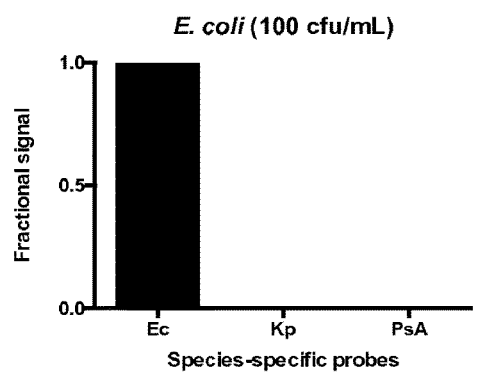

When whole blood spiked with 1000 cfu/mL of *E. coli* and diluted 1:3 in 1×PBS+0.1% BSA was assayed directly using Nanostring to detect bacterial rRNA, no discernable signal was detected above background (FIG. 10, middle panel, left figure, "Whole Blood"). When the eluent from this microfluidic device, containing the bacterial fraction separated from the majority of the red and white blood cells as described above, was assayed using Nanostring, a dominant signal from *E. coli*-reactive probes was readily detectable (FIG. 10, middle panel, right figure, "Spiral eluent"; the first three bars represent probes that recognize only *E. coli* [Ec], while the next four bars represent probes that recognize either *E. coli* or *K. pneumoniae* [Ec/Kp]; the next bar represents a probe that recognizes only *K. pneumoniae* [Kp], and the final 5 bars represent probes that recognize only *P. aeruginosa* [PsA]). Even when only 100 cfu/mL of *E. coli* was spiked into the blood prior to loading on the spiral device, the eluent (but not the pre-enriched blood sample) could be easily seen to contain *E. coli*, as computed by a transcriptional "organism score" represented by the fractional signal corresponding to probes that recognize only *E. coli*, divided by the sum total signal from all species-specific probes (FIG. 10, bottom panel).

Example 7

Method

This trial was carried out in a similar manner to Examples 5 and 6, but with more bacteria ($10^5$), and with detection designed to discern antibiotic susceptibility rather than mere species identification of the loaded bacteria. Only *E. coli* was used, but two different strains were tested, one of which was susceptible to the antibiotic ciprofloxacin, and the other of which was resistant to this antibiotic. A schematic of the experimental workflow for this example is shown in the top panel of FIG. 11. In the basic version of the test (FIG. 11, open circles or open triangles), $10^5$ cfu/mL of *E. coli* was spiked into whole blood, diluted 1:3 in 1×PBS+0.1% BSA, and then loaded on the spiral microfluidic device. The eluent was collected as described above, then exposed to antibiotic (ciprofloxacin) at 37° C. for 30 minutes. Antibiotic susceptibility was determined based on Nanostring measurements of mRNA transcripts whose expression level changes upon ciprofloxacin exposure in susceptible but not resistant *E. coli*. These mRNA results can be mathematically converted to a Transcriptional Score of antibiotic susceptibility, where susceptible strains have a score of 0 and resistant strains have a score around 1, using a method described in Barczak A K, Gomez J E et al, *Proc. Nat'l. Acad. Sci. USA* 2012; 109:6217 and further optimized.

In an extension of this test that more directly mimics a clinical positive blood culture (FIG. 11 stars), 50 cfu/mL of *E. coli* (either susceptible or resistant to ciprofloxacin) was spiked into a BacTec blood culture bottle of the sort used in clinical microbiology laboratories that contains bacterial growth media, which we had previously loaded with 10 mL of human blood obtained from a healthy donor. This spiked blood culture bottle was then allowed to incubate at 37° C. with shaking for 7 hours, a time previously noted to allow expansion of these 50 cfu/mL of *E. coli* to an abundance equivalent to that which would be measured as a positive blood culture in a clinical BacTec culture chamber. This final abundance was confirmed to be $10^7$ cfu/mL. 1 mL of this positive blood culture was loaded directly onto the spiral microfluidic device (without dilution into PBS+BSA, since the prior dilution into the BacTec culture media was sufficient to permit separation using the spiral device) and separated as described above. Once again, the bacterial elution fraction from the spiral device was analyzed using the Nanostring assay to detect the same mRNA transcripts whose expression level changes upon ciprofloxacin exposure in susceptible but not resistant *E. coli*, then converted to a Transcriptional Score as above.

As a control for both versions of this test, the same species of *E. coli* (both ciprofloxacin susceptible and resistant) were grown in pure axenic culture as described in Barczak A K, Gomez J E et al, *Proc. Nat'l. Acad. Sci. USA* 2012; 109: 6217, exposed to ciprofloxacin as above, and measured using the same Nanostring assay.

Results

Figure 11:
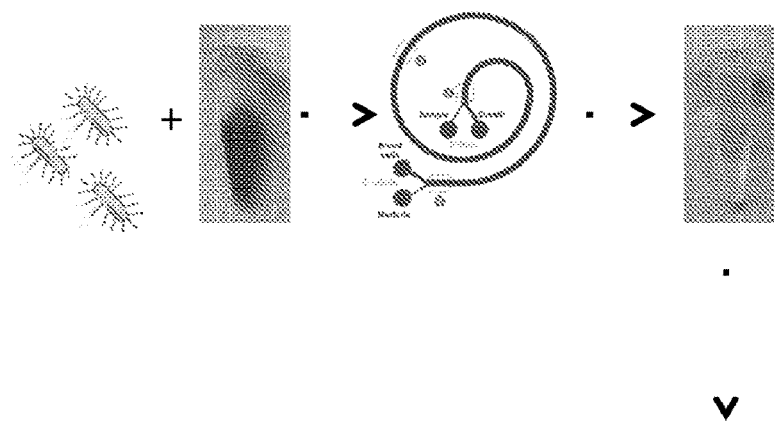
FIG. 11 shows the use high throughput microbe isolation microfluidic device for antibiotic susceptibility detection by mRNA identification on a Nanostring® platform. Using the disclosed device, antibiotic resistance in bacteria can be made at a concentration at least as low as $10^5$ cfu/mL.
Figure 11:
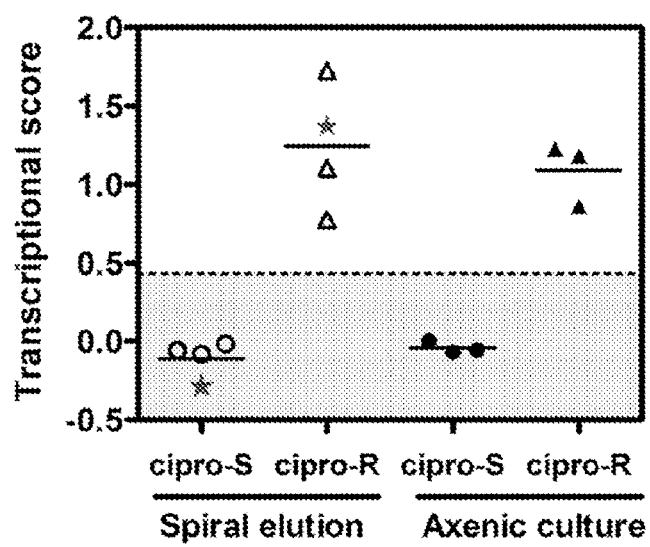

FIG. 11 displays the results of the above tests, showing that the bacterial elution fraction from the spiral device, using samples at or substantially below the typical concentration reached by bacterial cultures in a clinical BacTec blood culture system, faithfully reflected the antibiotic susceptibility of the strains in question. Results from the control experiment, in which the susceptible and resistant strains grown in axenic culture and not subjected to the spiral device, are shown in solid circles (ciprofloxacin-susceptible) or solid triangles (ciprofloxacin resistant); as described in Barczak A K, Gomez J E et al, *Proc. Nat'l. Acad. Sci. USA* 2012; 109:6217, these two strains can be readily distinguished by Transcriptional Score (y-axis). Similarly, data from the spiked blood samples (open circles and triangles) and the spiked blood culture bottles (stars) that were enriched using the spiral microfluidic device were also clearly identifiable as either susceptible or resistant based only on Transcriptional Score after the Nanostring assay. Such a result would be impossible out of blood samples without the enrichment and separation from host material provided by the spiral microchannel device.

We claim:

1. A method of isolating one or more microbes from a blood sample comprising red blood cells and leukocytes, the method comprising:
   introducing the blood sample into a sample inlet of a microfluidic device having at least one spiral channel wherein the at least one spiral channel having: a first end; a second end; a channel height; a channel width; and a channel length; and
   introducing a second fluid into a sheath inlet of the microfluidic device at a flow rate at least 5 to 10 times of the blood sample flow rate, wherein the spiral channel terminates in a microbe outlet and a waste outlet, wherein:
   the sample inlet having a width of 75 µm and the sheath inlet having a width of 425 µm;
   the microbe outlet having a width of 200 µm and the waste outlet having a width of 300 µm;
   the channel width is 500 µm; and
   the channel length is between 5 cm and 20 cm, and
   wherein the spiral channel comprises a length, height, and a width that define an aspect ratio adapted to isolate any microbes present in the sample along a first portion of the spiral channel terminating at the microbe outlet, and to isolate red blood cells and leukocytes along a second portion of the spiral channel terminating at the waste outlet; and
   collecting the microbes from the microbe outlet, thereby isolating the microbes.

2. The method of claim 1, wherein the spiral channel is 10 cm in linear length.

3. The method of claim 1, wherein the spiral channel has a channel height of 50 µm to 120 µm.

4. The method of claim 1, wherein the at least one or more spiral channels of the microfluidic device are arranged to form at least 1.0 spiral.

5. A device for detecting and/or separating microbes in a sample comprising red blood cells and leukocytes, the device comprising:
   at least one spiral channel having: a first end; a second end; a channel height; a channel width; and a channel length, wherein:
   the first end comprising a sample inlet and a sheath inlet,
   the sample inlet having a width of 75 µm and the sheath inlet having a width of 425 µm;
   the second end comprising a microbe outlet and a waste outlet,
   the microbe outlet having a width of 200 µm and the waste outlet having a width of 300 µm;
   the channel height is 50 µm to 120 µm;
   the channel width is 500 µm; and
   the channel length is between 5 cm and 20 cm, and
   wherein the spiral channel has a length, height, and a width that define an aspect ratio adapted to isolate any microbes present in the sample along a first portion of the spiral channel and to isolate red blood cells and leukocytes along a second portion of the spiral channel, whereby separated microbes from the sample are recovered at the microbe outlet.

6. The device of claim 5, wherein the channel is 10 cm in linear length; the channel has a height of 80 µm; and/or the one or more spiral channels of the microfluidic device are arranged to form at least 1.5 spirals.

7. The device of claim 5, wherein the one or more spiral channels of the microfluidic device are arranged to form at least 1.0 spirals.

8. The device of claim 5, wherein the one or more spiral channels have a radius of curvature between 0.3 to 1.5 cm.

9. The device of claim 5, wherein the sample is whole blood or blood fraction.

10. The device of claim 5, wherein the microbe recovery is at least 65%.

11. The device of claim 5, wherein the sample further comprises platelets that are recovered with an efficiency of 40%.

12. The device of claim 5, wherein the microbes are isolated along the radially outermost portion of the spiral channel to the microbe outlet.

13. The device of claim 5, wherein the leukocytes and/or red blood cells are isolated along the radially innermost portion of the spiral channel to the waste outlet.

14. The device of claim 5, wherein the microbes undergo a single Dean cycle migration prior to exiting the channel at the microbe outlet.

15. The device of claim 5, wherein the spiral channel has an aspect ratio of diameter to channel height between 0.1 and 0.5.

16. The device of claim 5, wherein the aspect ratio of the leukocytes and/or red blood cells to channel height is 0.05 to 0.2.

17. The device of claim 5, wherein where the aspect ratio of microbe diameter to channel height is less than 0.05.

18. The device of claim 5, wherein the microbe comprises one or more of *Enterococus faecium, Acinetobacter baumanii, Enterobacter* species, *Escherichia coli, Pseudomonas aeruginosa, Klebsiella pneumoniae, Stenotrophomonas maltophilia, Mycobacterium tuberculosis* or *Staphylococcus aureus*.

19. The device of claim 5, wherein the sample is introduced into the sample inlet at a rate of between 125 μL/min to 175 μL/min and a second fluid is introduced into the sheath inlet at a rate of 1.25 mL/min to 1.75 mL/min.

20. The device of claim 19, wherein the second fluid is phosphate buffered saline (PBS).

21. The device of claim 5, wherein the microbes are less than 3 μm in size.

22. The device of claim 5, wherein the microbes are analyzed after isolation.

23. The device of claim 22, wherein analyzing the microbes comprises identifying the microbes and/or determining if the microbes are resistant to one or more antibiotics.

24. The device of claim 22, wherein analyzing the microbes comprises analyzing rRNA and/or mRNA of the microbes to determine microbe identity and/or antibiotic resistance.

25. The device of claim 5, wherein the microbe recovery is at least 75%.

* * * * *

UNITED STATES PATENT AND TRADEMARK OFFICE
CERTIFICATE OF CORRECTION

PATENT NO. : 10,077,462 B2
APPLICATION NO. : 14/775341
DATED : September 18, 2018
INVENTOR(S) : Han Wei Hou et al.

Page 1 of 1

It is certified that error appears in the above-identified patent and that said Letters Patent is hereby corrected as shown below:

On the Title Page

Item (71) the Applicant:
Please change "THE GENERAL HOSPITAL CORP" to --THE GENERAL HOSPITAL CORPORATION--

Signed and Sealed this
Twenty-sixth Day of February, 2019

Andrei Iancu
*Director of the United States Patent and Trademark Office*